(12) United States Patent
Vogelbaum (10) Patent No.: US 11,324,936 B2
(45) Date of Patent: May 10, 2022

(54) SYSTEM AND METHOD FOR DELIVERING FLUID INTERNALLY OF A PATIENT'S BODY

(71) Applicant: THE CLEVELAND CLINIC FOUNDATION, Cleveland, OH (US)

(72) Inventor: Michael A. Vogelbaum, Moreland Hills, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 536 days.

(21) Appl. No.: 16/301,527

(22) PCT Filed: May 5, 2017

(86) PCT No.: PCT/US2017/032655
§ 371 (c)(1),
(2) Date: Nov. 14, 2018

(87) PCT Pub. No.: WO2017/200919
PCT Pub. Date: Nov. 23, 2017

(65) Prior Publication Data
US 2019/0290895 A1  Sep. 26, 2019

Related U.S. Application Data

(60) Provisional application No. 62/336,846, filed on May 16, 2016.

(51) Int. Cl.
*A61M 39/02* (2006.01)
*A61M 39/22* (2006.01)
(Continued)

(52) U.S. Cl.
CPC ........ *A61M 39/0208* (2013.01); *A61M 39/12* (2013.01); *A61M 39/223* (2013.01);
(Continued)

(58) Field of Classification Search
CPC .......... A61M 39/0208; A61M 39/0247; A61M 2039/0214; A61M 2039/0205;
(Continued)

(56) References Cited

U.S. PATENT DOCUMENTS 4,802,885 A * 2/1989 Weeks .............. A61M 39/0208
604/132
8,025,639 B2 * 9/2011 Powers .................. A61B 6/481
604/131
(Continued)

FOREIGN PATENT DOCUMENTS

WO  2007/093778 A1  8/2007

OTHER PUBLICATIONS

PCT International Search Report for corresponding International Application Serial No. PCT/US2017/032655, dated Aug. 1, 2017, pp. 1-15.

*Primary Examiner* — Rebecca E Eisenberg
*Assistant Examiner* — Tania Ismail
(74) *Attorney, Agent, or Firm* — Tarolli, Sundheim, Covell & Tummino LLP (57) ABSTRACT

A fluid distribution system for delivering fluid internally of a body comprises a hollow needle and an implantable access port. The needle has a tip with a predetermined shape. The access port includes (a) a housing that includes at least two fluid outlets, (b) a septum received in the housing, and (c) a valve member rotatable in the housing. The valve member includes valve fluid inlet and outlet openings and a valve inlet passage extending from the inlet opening to the outlet opening. The valve inlet passage has a shape complementary to the shape of the needle tip. The valve member is rotatable into (i) a first position in which the valve fluid outlet opening communicates with a first housing fluid outlet and (ii) a
(Continued)

second position in which the valve fluid outlet opening communicates with a second housing fluid outlet.

18 Claims, 3 Drawing Sheets

(51) Int. Cl.
*A61M 39/12* (2006.01)
*A61B 90/10* (2016.01)
*A61M 5/142* (2006.01)
*A61M 39/26* (2006.01)

(52) U.S. Cl.
CPC .... *A61B 2090/103* (2016.02); *A61M 5/14216* (2013.01); *A61M 39/0247* (2013.01); *A61M 39/22* (2013.01); *A61M 39/26* (2013.01); *A61M 2039/0205* (2013.01); *A61M 2039/0214* (2013.01); *A61M 2039/0261* (2013.01); *A61M 2039/0276* (2013.01); *A61M 2039/0282* (2013.01); *A61M 2039/229* (2013.01); *A61M 2210/0693* (2013.01)

(58) Field of Classification Search
CPC .. A61M 2039/0282; A61M 2039/0261; A61M 2039/0276; A61M 39/223; A61M 39/22; A61M 39/26; A61M 2039/229; A61M 5/14216

See application file for complete search history.

(56) References Cited

U.S. PATENT DOCUMENTS

| | | |
|---|---|---|
| 2005/0080401 A1 | 4/2005 | Peavey |
| 2012/0310182 A1 | 12/2012 | Fielder et al. |
| 2014/0276345 A1 | 9/2014 | Silin |

* cited by examiner

SYSTEM AND METHOD FOR DELIVERING FLUID INTERNALLY OF A PATIENT'S BODY

RELATED APPLICATION

This application claims priority from U.S. Provisional Patent Application Ser. No. 62/336,846, filed 16 May 2016. The subject matter of the aforementioned application is hereby incorporated by reference in its entirety.

FIELD OF THE INVENTION

The present invention relates to a system and a method for delivering fluid internally of a patient's body and, more particularly, to a fluid distribution system in which a valve is rotated by a needle and to a method of delivering fluid internally of a patient's body with such a system.

BACKGROUND OF THE INVENTION

Catheters are often implanted in patients to deliver therapeutic fluids over extended periods of time. If multiple sites in the patient's body need to be treated, multiple catheters and, typically, multiple fluid pumps are required. Although the use of a single pump may have some practical advantages in such a situation, the rate of flow of the therapeutic fluid to each site must either be predetermined and fixed or be controlled by the addition of one or more flow control valves.

SUMMARY OF THE INVENTION

The present invention is directed to a system and a method for delivering fluid internally of a body and, more particularly, to a fluid distribution system in which a valve is rotated by a needle and to a method of delivering fluid internally of a body with such a system.

In accordance with an embodiment of the present invention, a fluid distribution system for delivering fluid internally of a body of a patient comprises a hollow needle and an implantable access port. The needle has a tip with a predetermined shape. The access port includes (a) a housing that includes at least two housing fluid outlets, (b) a septum received in the housing, and (c) a valve member received in the housing. The valve member is rotatable relative to the housing and includes a valve fluid inlet opening and a valve fluid outlet opening. The valve member also includes a valve inlet passage extending from the valve fluid inlet opening through the valve member to the valve fluid outlet opening. At least a portion of the valve inlet passage has a predetermined shape that is complementary to the predetermined shape of the tip of the hollow needle. The valve inlet passage is dimensioned to receive the tip of the needle. The valve member is rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets. The valve member also is rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets.

In accordance with another embodiment of the present invention, an implantable access port comprises (a) a housing that includes at least two housing fluid outlets, (b) a septum received in the housing, and (c) a valve member received in the housing. The valve member is rotatable relative to the housing and includes a valve fluid inlet opening and a valve fluid outlet opening. The valve member also includes a valve inlet passage extending from the valve fluid inlet opening through the valve member to the valve fluid outlet opening. The valve member is rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets. The valve member also is rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets.

In accordance with a further embodiment of the present invention, a method of delivering fluid internally of a body of a patient comprises the step of implanting in the patient an access port. The access port comprises a housing that includes at least two housing fluid outlets, a septum received in the housing, and a valve member received in the housing. The valve member is rotatable relative to the housing and includes a valve fluid inlet opening and a valve fluid outlet opening. The valve member also includes a valve inlet passage extending from the valve fluid inlet opening through the valve member to the valve fluid outlet opening. At least a portion of the valve inlet passage has a predetermined shape. The valve member is rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets. The valve member also is rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets. The method also comprises the step of inserting a hollow needle into the access port. The needle includes a tip with a predetermined shape that is complementary to the predetermined shape of the at least a portion of the valve inlet passage of the valve member. The needle is inserted into the access port such that the tip of the needle is received in the at least a portion of the valve inlet passage of the valve member. The method further includes the step of rotating the needle while the tip of the needle is received in the at least a portion of the valve inlet passage of the valve member to rotate the valve member relative to the housing of the access port so that the valve member is rotated into the first position. The method still further includes the step of delivering a flow of fluid to the hollow needle so that the fluid flows through the needle and out of the valve fluid outlet opening to the first one of the at least two housing fluid outlets.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION

Figure 1:
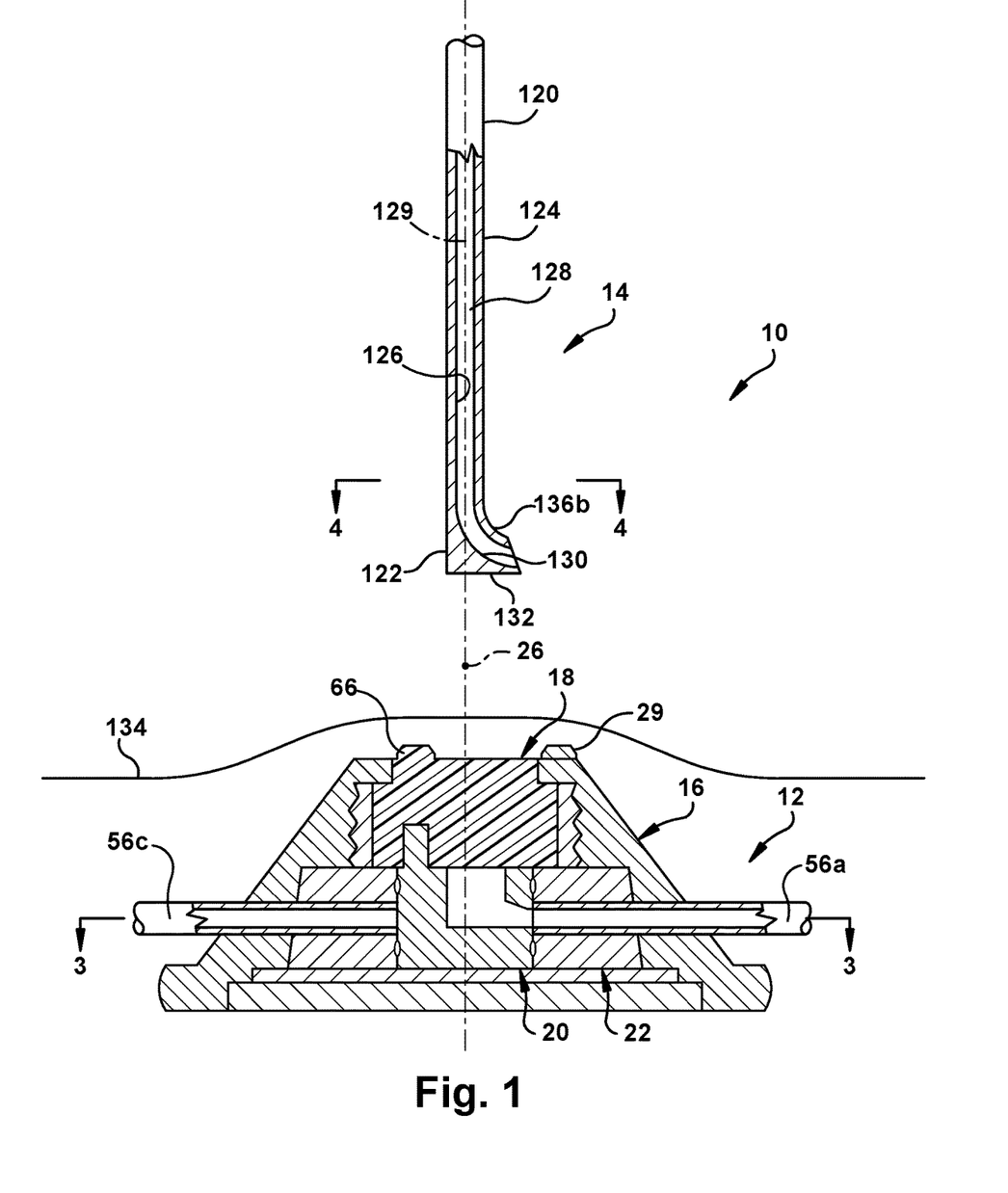
FIG. 1 is a side sectional view of a fluid delivery system in accordance with an embodiment of the present invention.

FIG. 1 illustrates a fluid distribution system 10 for delivering fluid internally of a body of a patient, which may be a human or another animal or any other organism, in accordance with an example of the present invention. The fluid distribution system 10 comprises an implantable access port 12 and a hollow needle 14.

The implantable access port 12 includes a housing 16, a septum 18, a rotatable valve member 20, and a stationary valve member 22. The septum 18, the rotatable valve member 20, and the stationary valve member 22 are all received in and retained in the housing 16.

Figure 2:
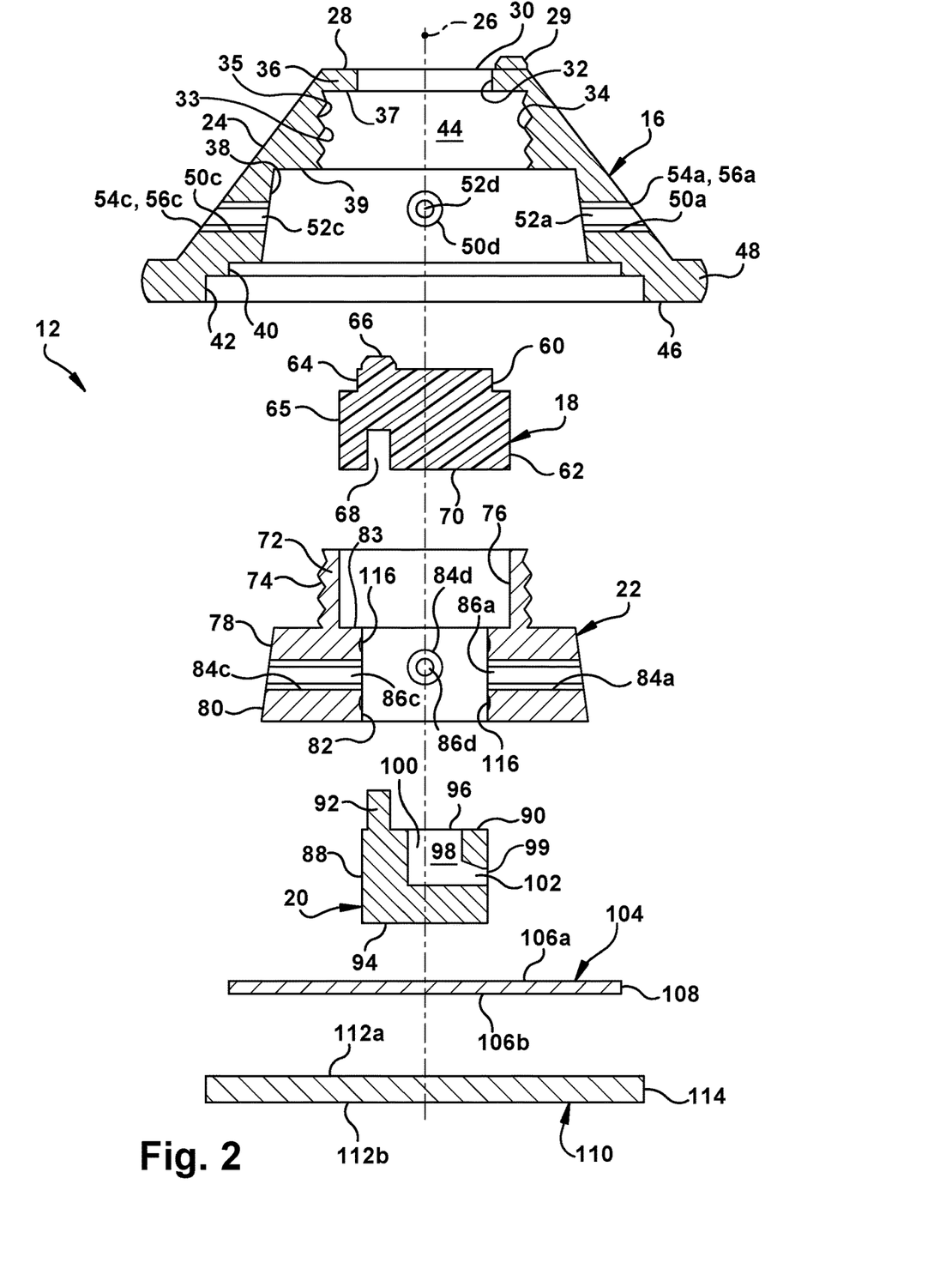
FIG. 2 is an exploded view of the access port of the fluid delivery system of FIG. 1.

As best shown in FIG. 2, the housing 16 is hollow and has a frustoconical outer shape. The housing may be formed of any biocompatible material, such as a biocompatible metal or polymer. An outer side surface 24 of the housing 16 defines a frustum of a cone that has a central longitudinal axis 26. The central longitudinal axis 26 is also the central longitudinal axis of the housing 16 and of the implantable access port 12. The top surface 28 of the housing 16 is flat, except for a raised indicator 29 that projects upward away from the housing. The top surface 28 surrounds and defines a circular central opening 30 in the top surface and the housing 16. A short cylindrical internal surface 32 of the housing 16 extends away from the top surface 28 and downward as viewed in FIG. 2. The central opening 30 and the cylindrical internal surface 32 both have the same diameter. Below the cylindrical internal surface 32, as viewed in FIG. 1, the housing has a threaded internal surface 34. The minimum diameter of the threaded internal surface 34, as defined by the ridges 33 of the threads, is greater than the diameter of the cylindrical internal surface 32. A radially extending surface 37 extends from the threaded internal surface 34 to the cylindrical internal surface 32. Consequently, the top surface 28, the cylindrical internal surface 32, and the radially extending surface 37 together help to define a radially inwardly extending lip 36 at the top of the housing 16.

Below the threaded internal surface 34 of the housing 16, as viewed in FIG. 2, the housing has a frustoconical internal surface 38. The minimum diameter of the frustoconical internal surface 38, which is at the top of the frustoconical internal surface, is greater than the maximum diameter of the threaded internal surface 34, which is defined by the grooves 35 of the threads. A radially extending surface 39 extends from the threaded internal surface 34 to the frustoconical internal surface 38. Below the frustoconical internal surface 38 of the housing 16, as viewed in FIG. 2, the housing has a short cylindrical internal seal surface 40. The diameter of the internal seal surface 40 is greater than the maximum diameter of the frustoconical internal surface 38, which maximum diameter is at the bottom of the frustoconical internal surface. Below the internal seal surface 40 of the housing 16, as viewed in FIG. 2, the housing has a short cylindrical internal closure surface 42. The diameter of the internal closure surface 42 is greater than the diameter of the internal seal surface 40. Together, the cylindrical internal surface 32, the radially extending surface 37, the threaded internal surface 34, the radially extending surface 39, the frustoconical internal surface 38, the internal seal surface 40, and the internal closure surface 42 partially define an interior space 44 within the housing 16 for receiving the septum 18, the rotatable valve member 20, and the stationary valve member 22.

The internal closure surface 42 of the housing 16 adjoins and intersects a flat bottom surface 46 of the housing. The flat bottom surface 46 extends radially outward away from the internal closure surface 42 and the central longitudinal axis 26. The flat bottom surface 46 extends radially outward beyond the maximum diameter of the frustoconical outer side surface 24 of the housing. As a result, the flat bottom surface 46 partially defines a radially outwardly extending lip 48, which is at the bottom of the frustoconical outer side surface 24.

Figure 3:
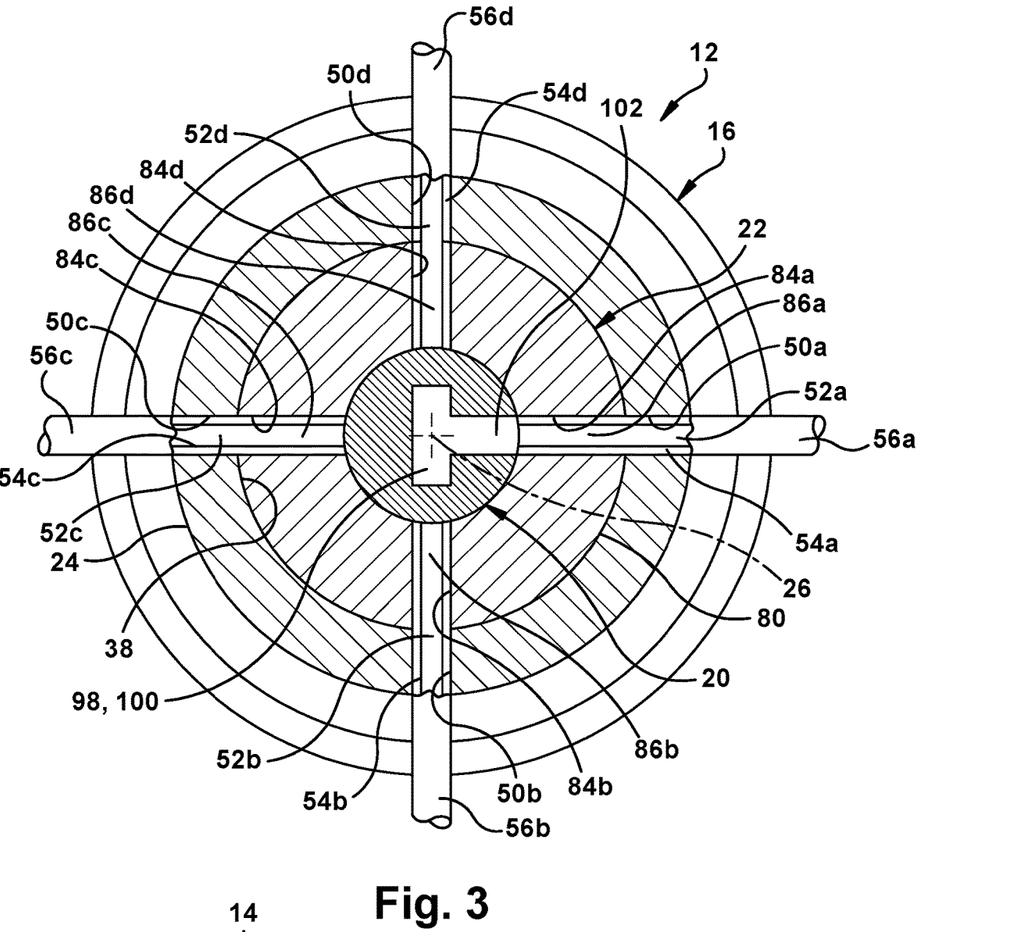
FIG. 3 is a sectional view taken in the direction of view line 3-3 of FIG. 1.

Four cylindrical surfaces 50a to 50d (only three of which are shown in FIG. 2) extend radially through the housing 16 from the frustoconical internal surface 38 to the frustoconical outer side surface 24. The radially extending cylindrical surfaces 50a-d define four radially extending outlets or outlet passages 52a-d that connect the interior space 44 of the housing 16 with the external environment surrounding the housing. The radially extending cylindrical surfaces 50a-d and outlet passages 52a-d are arrayed at 90° intervals about the circumference of the housing 16, as best seen in FIG. 3. One of the radially extending cylindrical surfaces 50a-d (specifically, the radially extending cylindrical surface 50a) and thus one of the outlet passages 52a-d is located directly below the raised indicator 29. Each of the outlet passages 52a-d receives an end portion 54a-d of a different piece 56a-d of tubing. The outlet passages 52a-d and the tubing pieces 56a-d thus define four fluid outlets from the housing 16. The tubing pieces 56a-d may be formed of any biocompatible material, such as a biocompatible polymer. The tubing pieces 56a-d may be catheters for delivering therapeutic liquids from the implantable access port 12 to different sites within a patient's body.

The septum 18 is received in the housing 16 adjacent the lip 36. The septum 18 is generally cylindrical in shape with two different outer diameters. One end portion 60 of the septum 18, which is the upper end portion as viewed in FIG. 2, has an outer diameter that is the same or substantially the same as the diameter of the cylindrical internal surface 32 of the housing 16 and the diameter of the central opening 30 in the housing. The length or height of the upper end portion 60, as measured in a direction parallel to the central longitudinal axis 26, is generally the same as the length or height of the cylindrical internal surface 32, as measured in a direction parallel to the central longitudinal axis 26. The opposite end portion 62 of the septum 18, which is the lower end portion as viewed in FIG. 2, has an outer diameter that is greater or larger than the diameter of the cylindrical internal surface 32 of the housing 16 and the diameter of the central opening 30 in the housing, but less or smaller than the minimum diameter of the threaded internal surface 34.

As a result of the configuration and dimensions of the septum 18, when the septum is inserted into the housing 16, the lower end portion 62 of the septum abuts the lip 36 of the housing. The upper end portion 60 of the septum 18 fills the central opening 30 in the top surface 28 of the housing 16, and an outer circumferential surface 64 of the upper end portion 60 seals against the cylindrical internal surface 32 of the housing. A raised indicator 66 projects upward away from the upper end portion 60 of the septum 18, as viewed in FIG. 2. A cylindrical socket 68 is formed in the lower end portion 62 of the septum 18. The socket 68 is offset radially from the central longitudinal axis 26 and has a closed upper end and an open lower end. The lower end of the socket 68 opens onto a substantially flat bottom surface 70 of the lower end portion 62. The septum 18 may be formed of any biocompatible material, such as a silicone elastomer, which can be repeatedly punctured by insertion of a needle and also seal against the needle, when present, and close the puncture when the needle is removed.

The stationary valve member 22 is received in the housing 16 adjacent the septum 18. One end portion 72 of the stationary valve member 22, which is the upper end portion as viewed in FIG. 2, has an outer circumferential surface 74 that is threaded so as to engage and be screwed into the threaded internal surface 34 of the housing 16. The diameter of the outer circumferential surface 74 of the upper end portion 72 of the stationary valve member 22 is therefore essentially the same as the diameter of the threaded internal surface 34 of the housing 16. The length or height of the upper end portion 72, as measured in a direction parallel to the central longitudinal axis 26, is the same or substantially the same as the length or height of the threaded internal surface 34, as measured in a direction parallel to the central longitudinal axis 26. The upper end portion 72 also has an internal cylindrical surface 76 that extends parallel to the central longitudinal axis 26 and that defines an internal passage through the upper end portion. The internal cylindrical surface 76 has a diameter that is the same or substantially the same as the diameter of the outer circumferential surface 65 of the lower end portion 62 of the septum 18.

The opposite end portion 78 of the stationary valve member 22, which is the lower end portion as viewed in FIG. 2, has a frustoconical outer circumferential surface 80 with an outer diameter at each point along the length or height of the frustoconical outer circumferential surface 80 that is the same or substantially the same as the diameter of the frustoconical internal surface 38 of the housing 16 at the corresponding point along the length or height of the frustoconical internal surface 38. The outer circumferential surface 80 of the stationary valve member 22 will thus fit closely against and seal against the frustoconical internal surface 38 of the housing 16. The lower end portion 78 also has an internal cylindrical surface 82 that extends parallel to the central longitudinal axis 26 and that defines an internal passage through the lower end portion. The internal cylindrical surface 82 has an inner diameter that is smaller or less than the diameter of the internal cylindrical surface 76 and the same or substantially the same as an outer diameter of the rotatable valve member 20. As a consequence of the difference in the diameters of the internal cylindrical surface 82 and the internal cylindrical surface 76, a radially extending surface 83 extends from the internal cylindrical surface 82 to the internal cylindrical surface 76.

When the stationary valve member 22 is inserted into the housing 16, the threaded outer circumferential surface 74 of the upper end portion 72 of the stationary valve member 22 engages and screws into the threaded internal surface 34 of the housing. The internal cylindrical surface 76 of the upper end portion 72 abuts and seals against the outer circumferential surface 65 of the lower end portion 62 of the septum 18. The frustoconical outer circumferential surface 80 of the lower end portion 78 of the stationary valve member 22 abuts and seals against the frustoconical internal surface 38 of the housing 16. A portion of the bottom surface 70 of the septum 18 also rests on the radially extending surface 83 of the lower end portion 78 of the stationary valve member 22. The stationary valve member 22 may be formed of any biocompatible material, such as a biocompatible metal or polymer, which can seal against the septum 18 and the housing 16.

Four cylindrical surfaces 84a to 84d (only three of which are shown in FIG. 2) extend radially through the stationary valve member 22 from the internal cylindrical surface 82 of the lower end portion 78 to the frustoconical outer circumferential surface 80 of the lower end portion 78. The radially extending cylindrical surfaces 84a-d define four passages 86a-d that also extend radially through the stationary valve member 22 from the internal cylindrical surface 82 of the lower end portion 78 to the frustoconical outer circumferential surface 80 of the lower end portion 78. The radially extending cylindrical surfaces 84a-d and passages 86a-d are arrayed at 90° intervals about the circumference of the stationary valve member 22, as best seen in FIG. 3. Each of the passages 86a-d is axially aligned with and communicates with a corresponding outlet passage 52a-d in the housing 16. Like the outlet passages 52a-d, each of the passages 86a-d also receives an end portion 54a-d of a different piece 56a-d of tubing. The passages 86a-d, the outlet passages 52a-d, and the tubing pieces 56a-d thus cooperate to define four fluid outlets from the access port 12.

The rotatable valve member 20 is also received in the housing 16 adjacent the septum 18. The rotatable valve member 20 may be formed of any biocompatible material, such as a biocompatible metal or polymer. The rotatable valve member 20 has an outer circumferential surface 88 that extends parallel to the central longitudinal axis 26. The outer circumferential surface 88 is cylindrical in shape and has a diameter that is the same or substantially the same as the diameter of the internal cylindrical surface 82 of the stationary valve member 22. The length or height of the rotatable valve member 20, as measured in a direction parallel to the central longitudinal axis 26, is the same or substantially the same as the length or height of the internal cylindrical surface 82, as measured in a direction parallel to the central longitudinal axis 26. The top surface 90 of the rotatable valve member 20, as viewed in FIG. 2, is substantially flat, except for an upwardly extending, cylindrical post 92, which is radially offset from the central longitudinal axis 26. The bottom surface 94 of the rotatable valve member 20, as viewed in FIG. 2, is also substantially flat.

A valve fluid inlet opening 96 is formed in the top surface 90 of the rotatable valve member 20. The valve fluid inlet opening 96 communicates with a valve inlet passage 98 that extends downward from the top surface 90 toward the bottom surface 94. The valve inlet passage 98 does not intersect the bottom surface 94 of the rotatable valve member 20, but instead turns and extends radially outward and intersects the outer circumferential surface 88 of the rotatable valve member 20. At the outer circumferential surface 88, the valve inlet passage 98 communicates with a valve fluid outlet opening 99. As best seen in FIG. 2, the valve inlet passage 98 has a shape resembling an "L," when viewed in cross-section taken radially of the central longitudinal axis 26 in a plane that includes the central longitudinal axis. As best seen in FIG. 3, the valve inlet passage 98 has a shape resembling a "T," when viewed in cross-section taken radially of the central longitudinal axis 26 in a plane that is perpendicular to the central longitudinal axis and parallel to the top surface 90. As also shown in FIG. 3, a first portion 100 of the valve inlet passage 98, which surrounds the central longitudinal axis 26, has a width that is greater than the width of a second portion 102 of the valve inlet passage that extends radially outward to the outer circumferential surface 88 of the rotatable valve member 20.

When the rotatable valve member 20 is received in the housing 16, the top surface 90 of the rotatable valve member is positioned so as to abut against the bottom surface 70 of the septum 18. The post 92 of the rotatable valve member 20 is received in the socket 68 of the septum. The post 92 and the socket 68 are both offset radially from the central longitudinal axis 26 by the same distance. The outer circumferential surface 88 of the rotatable valve member 20 is positioned in abutting relationship with or against the internal cylindrical surface 82 of the stationary valve member 22. At the outer circumferential surface 88, depending on the rotational position of the rotatable valve member 20 about or around the central longitudinal axis 26, the second portion 102 of the valve inlet passage 98 may be aligned with and communicate with one of the passages 86a-d and a corresponding one of the tubing pieces 56a-d in the stationary valve member 22.

To seal the bottom surface 94 of the rotatable valve member 20 within the housing 16, a disc-shaped seal element 104 is received in the housing adjacent the bottom surface 94 of the rotatable valve member. The seal element 104 has upper and lower substantially flat major side surfaces 106a and b, respectively. The seal element 104 also has a circular outer circumferential surface 108 that is larger in diameter than the largest portion of the frustoconical outer circumferential surface 80 of the lower end portion 78 of the stationary valve member 22. The outer circumferential surface 108 of the seal element 104 contacts and seals against the internal seal surface 40 of the housing 16. The seal element 104 thus seals against all three of the rotatable valve member 20, the stationary valve member 22, and the housing 16. The seal element 104 may be formed of any biocompatible material, such as a silicone elastomer, which can seal against the rotatable valve member 20, the stationary valve member 22, and the housing 16.

To hold or support the septum 18, the rotatable valve member 20, the stationary valve member 22, and the seal element 104 in the housing 16, a disc-shaped closure element 110 is received in the housing adjacent the seal element. The closure element 110 has upper and lower substantially flat major side surfaces 112a and b, respectively. The closure element 110 also has a circular outer circumferential surface 114 that is larger in diameter than the outer circumferential surface 108 of the seal element 104. The outer circumferential surface 114 of the closure element 110 engages or contacts the internal closure surface 42 of the housing 16. The closure element 110 may be formed of any biocompatible material, such as a biocompatible metal or polymer.

As will be appreciated, proper functioning of the implantable access port 12 requires that a fluid seal be provided between each of the surfaces of the housing 16, septum 18, rotatable valve member 20, stationary valve member 22, and seal element 104, and potentially the closure element 110, that contacts a surface of another component. The fluid seal may be achieved by having the contacting or abutting surfaces fit so closely against one another that fluid, particularly liquid, cannot pass between the surfaces. Alternatively, the materials of which the components and thus the abutting surfaces are made may be selected to provide sufficiently close conformance between the surfaces to provide a fluid seal. In many circumstances, a combination of the smoothness or finish of the abutting surfaces and the materials of which the surfaces are made will be used to achieve a desired level of sealing against fluid flow. Thus, for example, when a surface is described as "substantially flat," the required degree of flatness is the degree necessary to achieve, to the extent commercially practical, a fluid seal with an abutting "substantially flat" surface. As yet a further alternative, it may be necessary or desirable to provide a separate seal element, such as a sealing ring or gasket, between two abutting surfaces. Thus, in FIG. 2, optional grooves 116 are shown in the internal cylindrical surface 82 of the stationary valve member 22 to receive sealing rings (not shown). Still further, for abutting surfaces that do not move relative to one another, a sealing adhesive may be used.

When the access port 12 is fully assembled, the rotatable valve member 20 and the septum 18 are rotatable together relative to the housing 16, the stationary valve member 22, the seal element 104, and the closure element 110. As the rotatable valve member 20 rotates in a given direction, clockwise or counter-clockwise, around the central longitudinal axis 26, the valve fluid outlet opening 99 and the second portion 102 of the valve inlet passage 98 will move sequentially into and out of alignment with individual ones of the passages 86a-d and the corresponding tubing pieces 56a-d in the stationary valve member 22. Because the passages 86a-d are aligned with the outlet passages 52a-d in the housing 16 and because each of the corresponding tubing pieces 56a-d extends through a passage 86a-d and aligned outlet passage 52 a-d, the valve fluid outlet opening 99 and the second portion 102 of the valve inlet passage 98 will also move sequentially into and out of alignment with individual ones of the outlet passages 52a-d in the housing 16. The valve fluid outlet opening 99 and the second portion 102 of the valve inlet passage 98 may thus be aligned with and communicate with individual ones of the outlet passages 52a-d in the housing 16.

When, for example, the valve fluid outlet opening 99 and the second portion 102 of the valve inlet passage 98 in the fully assembled access port 12 rotate into alignment with the passage 86a and, therefore, also with the outlet passage 52a, the valve fluid outlet opening 99 communicates with the outlet passage 52a and fluid communication is established between the valve fluid inlet opening 96 and the outlet passage 52a. Fluid may thus flow from the valve fluid inlet opening 96, though the valve inlet passage 98, out through the valve fluid outlet opening 99, through the passage 86a in the stationary valve member 22, and to and into the outlet passage 52a in the housing 16. At the same time, the close fit between the outer circumferential surface 88 of the rotatable valve member 20 and the internal cylindrical surface 82 of the stationary valve member 22 blocks communication with each of the remaining passages 86b-d and corresponding outlet passages 52b-d. Fluid thus may not flow or is blocked from flowing from the valve fluid inlet opening 96, though the valve inlet passage 98, and out through the valve fluid outlet opening 99 into any of the remaining passages 86b-d and corresponding outlet passages 52b-d. As the valve fluid outlet opening 99 and the second portion 102 of the valve inlet passage 98 in the fully assembled access port 12 rotates out of alignment with the passage 86a and the outlet passage 52a and into alignment with, for example, the passage 86b and, therefore, also with the outlet passage 52b, the valve fluid outlet opening 99 communicates with the outlet passage 52b and fluid communication is established between the valve fluid inlet opening 96 and the outlet passage 52b. Fluid may thus flow from the valve fluid inlet opening 96, though the valve inlet passage 98, out through the valve fluid outlet opening 99, through the passage 86b in the stationary valve member 22, and to and into the outlet passage 52b in the housing 16. At the same time, the close fit between the outer circumferential surface 88 of the rotatable valve member 20 and the internal cylindrical surface 82 of the stationary valve member 22 blocks communication with each of the remaining passages 86a, c, and d and corresponding outlet passages 52a, c, and d. Fluid thus may not flow or is blocked from flowing from the valve fluid inlet opening 96, though the valve inlet passage 98, and out through the valve fluid outlet opening 99 into any of the remaining passages 86a, c, and d and corresponding outlet passages 52a, c, and d. Corresponding results will be produced when the valve fluid outlet opening 99 and the second portion 102 of the valve inlet passage 98 are rotated into alignment with each of the other passages 86c and d and corresponding outlet passages 52c and d.

Figure 4:
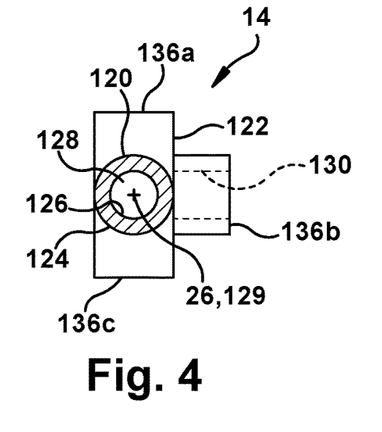
FIG. 4 is a sectional view taken in the direction of view line 4-4 of FIG. 1.

To achieve a flow of fluid into the valve fluid inlet opening 96, and also to rotate the rotatable valve member 20, the hollow needle 14 is inserted into the access port 12. As shown in FIG. 1, the hollow needle 14 has an elongated main body portion 120 and a terminal end portion 122 with a predetermined shape. As best seen in FIG. 4, the main body portion 120 of the hollow needle 14 has a cylindrical outer surface 124 and a substantially coaxial cylindrical inner surface 126. The cylindrical inner surface 126 defines a lumen 128 for the hollow needle 14. Within the main body portion 120 of the hollow needle 14, the lumen 128 is centrally located on a needle longitudinal axis 129, which may be aligned with the central longitudinal axis 26, as explained below. The cylindrical outer surface 124 may have any desired diameter, such as, for example, a diameter of a 21 gauge or 23 gauge needle.

The terminal end portion 122 of the hollow needle 14 has an outer shape that is complementary to and mates with the shape of the valve inlet passage 98 in the rotatable valve member 20. As can be seen in FIG. 4, the terminal end portion 122 has an outer shape resembling a "T" with three tangs 136a-c projecting radially outward from the needle longitudinal axis 129 and the lumen 128 of the hollow needle 14. The tangs 136a-c are circumferentially spaced apart from one another by predetermined angles, such as 90°. The terminal end portion 122 is also dimensioned to fit into the valve inlet passage 98.

As can be seen in FIG. 1, the terminal end portion 122 of the hollow needle 14 has an arcuate or bowed inner surface 130 that is a continuation of the cylindrical inner surface 126. The inner surface 130 thus defines an extension of the lumen 128, which turns radially outward to extend away from the main body portion 120 of the hollow needle 14. The inner surface 130 is formed in the center tang 136b of the T-shaped terminal end portion 122. The extension of the lumen 128 and the center tang 136b of the terminal end portion 122 both extend or project radially outward from the main body portion 120 for a predetermined and fixed distance equal to about one or two times the diameter of the cylindrical outer surface 124 of the main body portion. The bottom surface 132 of the terminal end portion 122 is sharpened, comes to a point, or is otherwise shaped to facilitate insertion of the hollow needle 14 through the skin 134 of a patient (not shown) to engage the implantable access port 12.

In use, the implantable access port 12 and the tubing pieces 56a-d are first implanted in the body of a patient. If the tubing pieces 56a-d are not fluid delivery catheters or if additional fluid delivery devices are connected to the distal ends (not shown) of the tubing pieces 56a-d, such catheters or additional fluid delivery devices (not shown) are also implanted where required in the body of the patient. As shown in FIG. 1, the implantable access port 12 is implanted so as to be entirely subcutaneous or entirely below the patient's skin 134.

When the patient's physician or other health care provider desires to have a liquid pharmaceutical compound or other therapeutic fluid delivered through the implantable access port to one or more of the sites within the patient's body to which the tubing pieces 56a-d are ultimately connected, the physician or other health care provider will pierce the patient's skin 134 with the sharpened bottom surface 132 of the terminal end portion 122 of the hollow needle 14. The proper point at which to pierce the patient's skin 134 is determined by palpating the skin to locate, for example, the raised indicator 66 on the septum 18. As will be explained below, the raised indicator 66 will always be in a predetermined orientation with respect to the second portion 102 of the valve inlet passage 98 in the rotatable valve member 20. Thus, when the physician or other health care provider locates the raised indicator 66 in relation to the remainder of the implantable access port 12, the physician or other health care provider will know where to pierce the patient's skin 134 and in which direction to present the center tang 136b of the terminal end portion 122 of the hollow needle 14. To aid in distinguishing the raised indicator 66 from the raised indicator 29, the raised indicator 66 and the raised indicator 29 may have different shapes.

When the physician or other health care provider pierces the patient's skin 134 with the terminal end portion 122 of the hollow needle 14, the physician or other health care provider will press the terminal end portion into the septum 18 of the implantable access port 12. If the terminal end portion 122 of the hollow needle 14 is properly aligned with the valve inlet passage 98, the terminal end portion will pass through the septum 18 and into the valve inlet passage. If the terminal end portion 122 of the hollow needle 14 is not properly aligned with the valve inlet passage 98, however, the terminal end portion will not be able to enter the valve inlet passage, and the physician or other health care provider will be able to detect that the terminal end portion is not moving sufficiently far into the implantable access port 12. The physician or other health care provider will then have to make minor rotational adjustments in the orientation of the hollow needle 14 and, more particularly, the center tang 136b of the terminal end portion 122 of the hollow needle in order to align the terminal end portion properly with the valve inlet passage 98. When proper alignment of the terminal end portion 122 and the valve inlet passage 98 is achieved, the physician or other health care provider will be able to seat the terminal end portion fully into the valve inlet passage.

With the terminal end portion 122 of the hollow needle 14 fully inserted in the valve inlet passage 98 and the needle longitudinal axis 129 aligned with the central longitudinal axis 26, the hollow needle can be rotated, as required, about the central longitudinal axis 26 until lumen 128 in the terminal end portion is aligned with and communicates with one of the radially extending cylindrical surfaces 84a-d and passages 86a-d. The proper alignment will be determined by locating the raised indicator 29 on the top surface 28 of the housing 16, which is located directly above one of the radially extending cylindrical surfaces 50a-d and outlet passages 52a-d. The radially extending cylindrical surfaces 50a-d and outlet passages 52a-d are aligned with the radially extending cylindrical surfaces 84a-d and passages 86a-d. As shown in FIG. 1, for example, the raised indicator 29 of the housing 16 is located diametrically across the housing from the raised indicator 66 on the septum 18. A liquid pharmaceutical compound or other therapeutic fluid may then be delivered from a reservoir (not shown) or other source to the lumen 128 of the hollow needle 14, through the lumen of the hollow needle, and into the particular radially extending passage 86a and tubing piece 56a that are aligned with the lumen in the terminal end portion 122 of the hollow needle. The liquid pharmaceutical compound or other therapeutic fluid may then be delivered though the tubing piece 56a and the corresponding outlet passage 52a to the site (not shown) within the patient's body to which the tubing piece leads.

It will be appreciated that when the center tang 136b of the terminal end portion 122 of the hollow needle 14, together with the second portion 102 of the valve inlet passage 98, is in alignment with one of the radially extending cylindrical surfaces 84a-d and passages 86a-d, such as the cylindrical surface 84a and the passage 86a, the outer circumferential surface 88 of the rotatable valve member 20 blocks communication with the remaining three radially extending cylindrical surfaces 84b-d and passages 86b-d. Thus, when the lumen 128 in the terminal end portion 122 of the hollow needle 14 is in communication with the passage 86a, the liquid pharmaceutical compound or other therapeutic fluid will flow from the hollow needle exclusively or solely through the passage 86a, the aligned outlet passage 52a, and the tubing piece 56a and will not flow through the remaining radially extending passages 86b-d, outlet passages 52b-d, and tubing pieces 56b-d.

When it is desired to direct the liquid pharmaceutical compound or other therapeutic fluid to one of the other three radially extending passages 86b-d, outlet passages 52b-d, and tubing pieces 56b-d, such as the passage 86b, the outlet passage 52b, and the tubing piece 56b, the physician or other health care provider can rotate the hollow needle 14 about the central longitudinal axis 26 until the center tang 136b of the terminal end portion 122 of the hollow needle is in alignment with the cylindrical surface 84b, the radially extending passage 86b, and the tubing piece 56b. Rotating the hollow needle 14 without removing the terminal end portion 122 from the valve inlet passage 98 will cause the rotatable valve member 20 to rotate relative to the lower end portion 78 of the stationary valve member 22 and the housing 16. At the same time, because the post 92 of the rotatable valve member 20 is received in the socket 68 of the septum 18, the septum will rotate together with the rotatable valve member relative to the upper end portion 72 of the stationary valve member 22. The raised indicator 66 of the septum 18 will move with the septum and relative to the raised indicator 29 on the housing 16. The relative movement of the raised indicators 66 and 29 will provide an indication of the alignment between (a) the terminal end portion 122 of the hollow needle 14 and (b) the cylindrical surface 84b, the passage 86b, and the tubing piece 56b.

When the lumen 128 in the terminal end portion 122 of the hollow needle 14 is aligned with the radially extending cylindrical surface 84b and communicates with the passage 86b, the liquid pharmaceutical compound or other therapeutic fluid may then be delivered from the lumen of the hollow needle and into the radially extending passage 86b, the aligned outlet passage 52d, and the tubing piece 56b. The liquid pharmaceutical compound or other therapeutic fluid may then be delivered though the tubing piece 56b to the site (not shown) within the patient's body to which the tubing piece leads. When the center tang 136b of the terminal end portion 122 of the hollow needle 14, together with the second portion 102 of the valve inlet passage 98, is in alignment with the cylindrical surface the passage 86b, the outer circumferential surface 88 of the rotatable valve member 20 blocks communication with the remaining three radially extending cylindrical surfaces 84a, c, and d and passages 86a, c, and d. Thus, when the lumen 128 in the terminal end portion 122 of the hollow needle 14 is in communication with the passage 86b, the liquid pharmaceutical compound or other therapeutic fluid will flow from the hollow needle exclusively or solely through the passage 86b, the aligned outlet passage 52b, and the tubing piece 56b and will not flow through the remaining three radially extending passages 86a, c, and d, outlet passages 52a, c, and d, and tubing pieces 56a, c, and d.

The steps set out above for communicating with the radially extending passages 86a and b, the outlet passages 52a and b, and the tubing pieces 56a and b may be carried out, as required, to deliver the liquid pharmaceutical compound or other therapeutic fluid from the hollow needle selectively through one or other of the passages 86c and d, the outlet passages 52c and d, and the tubing pieces 56c and d.

As the therapeutic fluid flows through the hollow needle 14 in contact with the inner surfaces 126 and 130 of the needle and into the passages 86a-d and outlet passages 52a-d, the therapeutic fluid is also flowing through the valve inlet passage 98 even though the therapeutic fluid may never contact any surface of the rotatable valve member 20. It is the rotational position of the rotatable valve member 20 and, therefore, the valve inlet passage 98 relative to the stationary valve member 22 and the housing 16 and, therefore, the passages 86a-d and corresponding outlet passages 52a-d that provides fluid communication with the outlet passages and that permits the flow of therapeutic fluid to the outlet passages.

Although the illustrated embodiment of FIGS. 1-4 incorporates a septum 18 that rotates within the stationary valve member 22 and the housing 16, the septum may alternatively remain stationary. Thus, for example, the socket 68 may be annular in shape, so that the post 92 of the rotatable valve member can travel around the annular socket. By making the portion of the septum 18 above such an annular socket 68 relatively thin, a physician or other health care provider may be able to palpate the implantable access port 12 and detect the position of the post 92 of the rotatable valve member 20. It may also or alternatively be desirable to change the external shape of the housing 16 so that the orientation of the housing and, therefore, the passages 86a-d and outlet passages 52a-d can be determined from the external shape of the housing 16, rather than from the position of the raised indicator 29. Further still, although the illustrated embodiment of the access port 12 comprises a housing 16 and a stationary valve member 22, which together facilitate assembly of the illustrated access port, it may also be possible or desirable to form the housing and the stationary valve member in one piece.

In addition, while the embodiment of FIGS. 1-4 is an entirely mechanical system in which the hollow needle 14 is inserted into the implantable access port 12 and then manually rotated, it is contemplated that a more automated system may be implemented with a microelectromechanical system ("MEMS"). With MEMS technology, once the hollow needle 14 is inserted into the valve inlet passage 98, rotation of the rotatable valve member 20 would be achieved through a MEMS motor controlled by the physician or other health care provider and/or by a timer and/or in response to feedback from an internal probe or external sensor in or on the patient. Such a system would permit selection of a treatment site and the dosage in a more automated manner.

Further, while a particular treatment site or sites may be anywhere within a patient's body, the embodiment of FIGS. 1-4 may be particularly beneficial for treatments applied to a patient's brain. In this regard, feedback from an internal probe or external sensor, whether used to control the position of the rotatable valve member 20 entirely mechanically or in an automated manner, may be feedback from an internal probe monitoring epilepsy electrical spikes.

From the above description of the invention, those skilled in the art will perceive improvements, changes and modifications. Such improvements, changes, and/or modifications within the skill of the art are intended to be covered by the appended claims.

Having described the invention, the following is claimed:

1. A fluid distribution system for delivering fluid internally of a body of a patient comprising:
   a hollow needle including a tip having a predetermined shape; and
   an implantable access port including
   (a) a housing that includes at least two housing fluid outlets,
   (b) a septum received in the housing, and
   (c) a valve member received in the housing, the valve member being rotatable relative to the housing and including a valve fluid inlet opening and a valve fluid outlet opening, the valve member also including a valve inlet passage extending from the valve fluid inlet opening through the valve member to the valve fluid outlet opening,
   at least a portion of the valve inlet passage having a predetermined shape that is complementary to the predetermined shape of the tip of the hollow needle, the valve inlet passage being dimensioned to receive the tip of the needle,
   the valve member being rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets, the valve member also being rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets.

2. A fluid distribution system according to claim 1 wherein the valve member is rotatable relative to the housing by rotating the needle when the tip of the needle is received in the at least a portion of the valve inlet passage.

3. A fluid distribution system according to claim 1 wherein the valve member when rotated into the first position permits fluid flow from the valve fluid inlet opening through the valve inlet passage and the valve fluid outlet opening into the first one of the at least two housing fluid outlets, the valve member when rotated into the second position permitting fluid flow from the valve fluid inlet opening through the valve inlet passage and the valve fluid outlet opening into the second one of the at least two housing fluid outlets.

4. A fluid distribution system according to claim 1 wherein the valve member when rotated into the first position blocks fluid flow from the valve fluid inlet opening through the valve inlet passage and the valve fluid outlet opening into a second one of the at least two housing fluid outlets, the valve member when rotated into the second position blocking fluid flow from the valve fluid inlet opening through the valve inlet passage and the valve fluid outlet opening into the first one of the at least two housing fluid outlets.

5. A fluid distribution system according to claim 1 wherein the housing includes multiple housing fluid outlets, the valve member being rotatable relative to the housing into a first position in which (i) the valve fluid outlet opening communicates with a first one of the multiple housing fluid outlets to permit a flow of fluid from the valve fluid outlet opening to the first one of the multiple housing fluid outlets and (ii) the valve member blocks all other ones of the multiple housing fluid outlets, the valve member also being rotatable relative to the housing into a second position in which (i) the valve fluid outlet opening communicates with a second one of the multiple housing fluid outlets to permit a flow of fluid from the valve fluid outlet opening to the second one of the multiple housing fluid outlets and (ii) the valve member blocks all other ones of the multiple housing fluid outlets, including the first one of the multiple housing fluid outlets.

6. A fluid distribution system according to claim 1 wherein each housing outlet includes a passage extending from an inner circumferential surface of the housing through the housing to an outer circumferential surface of the housing.

7. A fluid distribution system according to claim 1 wherein the access port also includes an indicator that marks a rotational orientation of the valve member relative to the housing, the indicator being perceptible by touch.

8. An implantable access port comprising:
   (a) a housing that includes at least two housing fluid outlets;
   (b) a septum received in the housing; and
   (c) a valve member received in the housing, the valve member being rotatable relative to the housing and including a valve fluid inlet opening and a valve fluid outlet opening, the valve member also including a valve inlet passage extending from the valve fluid inlet opening through the valve member to the valve fluid outlet opening,
   the valve member being rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets, the valve member also being rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets.

9. An implantable access port according to claim 8 wherein the valve member when rotated into the first position permits fluid flow from the valve fluid inlet opening through the valve inlet passage and the valve fluid outlet opening into the first one of the at least two housing fluid outlets, the valve member when rotated into the second position permitting fluid flow from the valve fluid inlet opening through the valve inlet passage and the valve fluid outlet opening into the second one of the at least two housing fluid outlets.

10. An implantable access port according to claim 8 wherein the valve member when rotated into the first position blocks fluid flow from the valve fluid inlet opening through the valve inlet passage and the valve fluid outlet opening into a second one of the at least two housing fluid outlets, the valve member when rotated into the second position blocking fluid flow from the valve fluid inlet opening through the valve inlet passage and the valve fluid outlet opening into the first one of the at least two housing fluid outlets.

11. An implantable access port according to claim 8 wherein the housing includes multiple housing fluid outlets, the valve member being rotatable relative to the housing into a first position in which (i) the valve fluid outlet opening communicates with a first one of the multiple housing fluid outlets to permit a flow of fluid from the valve fluid outlet opening to the first one of the multiple housing fluid outlets and (ii) the valve member blocks all other ones of the multiple housing fluid outlets, the valve member also being rotatable relative to the housing into a second position in which (i) the valve fluid outlet opening communicates with a second one of the multiple housing fluid outlets to permit a flow of fluid from the valve fluid outlet opening to the second one of the multiple housing fluid outlets and (ii) the valve member blocks all other ones of the multiple housing fluid outlets, including the first one of the multiple housing fluid outlets.

12. An implantable access port according to claim 8 wherein each housing outlet includes a passage extending from an inner circumferential surface of the housing through the housing to an outer circumferential surface of the housing.

13. An implantable access port according to claim 8 also including an indicator that marks a rotational orientation of the valve member relative to the housing, the indicator being perceptible by touch.

14. A method of delivering fluid internally of a body of a patient, the method comprising the steps of:
(a) implanting in the patient an access port comprising a housing that includes at least two housing fluid outlets, a septum received in the housing, and a valve member received in the housing, the valve member being rotatable relative to the housing and including a valve fluid inlet opening and a valve fluid outlet opening, the valve member also including a valve inlet passage extending from the valve fluid inlet opening through the valve member to the valve fluid outlet opening, at least a portion of the valve inlet passage having a predetermined shape, the valve member being rotatable relative to the housing into a first position in which (i) the valve fluid outlet opening communicates with a first one of the at least two housing fluid outlets to permit a flow of fluid from the valve fluid outlet opening to the first one of the at least two housing fluid outlets and (ii) the valve member blocks a second one of the at least two housing fluid outlets, the valve member also being rotatable relative to the housing into a second position in which (i) the valve fluid outlet opening communicates with the second one of the at least two housing fluid outlets to permit a flow of fluid from the valve fluid outlet opening to the second one of the at least two housing fluid outlets and (ii) the valve member blocks the first one of the at least two housing fluid outlets;
(b) inserting a hollow needle into the access port, the needle including a tip with a predetermined shape that is complementary to the predetermined shape of the at least a portion of the valve inlet passage of the valve member, the needle being inserted into the access port such that the tip of the needle is received in the at least a portion of the valve inlet passage of the valve member;
(c) rotating the needle while the tip of the needle is received in the at least a portion of the valve inlet passage of the valve member to rotate the valve member relative to the housing of the access port so that the valve member is rotated into the first position; and
(d) delivering a flow of fluid to the hollow needle so that the fluid flows through the needle and out of the valve fluid outlet opening to the first one of the at least two housing fluid outlets.

15. A method according to claim 14 wherein the step of rotating the needle while the tip of the needle is received in the at least a portion of the valve inlet passage of the valve member also includes rotating the valve member out of the first position and into the second position so that the fluid flows through the needle and out of the valve fluid outlet opening to the second one of the at least two housing fluid outlets.

16. A fluid distribution system according to claim 1 wherein
the valve inlet passage is T-shaped when viewed in cross-section in a plane substantially perpendicular to a central longitudinal axis of the housing, and
an outer shape of the tip of the hollow needle is T-shaped with three tangs projecting radially outward from a needle longitudinal axis of the hollow needle.

17. A fluid distribution system according to claim 1 wherein the septum is connected to the valve member and is rotatable with the valve member relative to the housing.

18. A fluid distribution system according to claim 1 wherein the implantable access port further includes a stationary valve member received in the housing, the stationary valve member having an upper end portion with a passage in which at least a portion of the septum is received and a lower end portion with a passage in which at least a portion of the valve member is received, the lower end portion having at least two fluid passages that each fluidly communicates with a corresponding housing fluid outlet,
the valve member being rotatable relative to the stationary valve member into the first position in which (i) the valve fluid outlet opening communicates with a first one of the at least two fluid passages of the stationary valve member to permit a flow of fluid from the valve fluid outlet opening to the first one of the at least two fluid passages of the stationary valve member and (ii) the valve member blocks a second one of the at least two fluid passages of the stationary valve member, the valve member also being rotatable relative to the housing into the second position in which (i) the valve fluid outlet opening communicates with the second one of the at least two fluid passages of the stationary valve member to permit a flow of fluid from the valve fluid outlet opening to the second one of the at least two fluid passages of the stationary valve member and (ii) the valve member blocks the first one of the at least two fluid passages of the stationary valve member.

\* \* \* \* \*